(12) United States Patent
Karl et al.

(10) Patent No.: US 9,695,139 B2
(45) Date of Patent: Jul. 4, 2017

(54) GLYCIDYL ETHERS OF LIMONENE DERIVATIVES AND OLIGOMERS THEREOF AS CURABLE EPOXY RESINS

(71) Applicant: BASF SE, Ludwigshafen (DE)

(72) Inventors: Ulrich Karl, Gruenstadt (DE); Monika Charrak, Ludwigshafen (DE); Hans-Josef Thomas, Korschenbroich (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/911,974

(22) PCT Filed: Jul. 30, 2014

(86) PCT No.: PCT/EP2014/066327
§ 371 (c)(1),
(2) Date: Feb. 12, 2016

(87) PCT Pub. No.: WO2015/022188
PCT Pub. Date: Feb. 19, 2015

(65) Prior Publication Data
US 2016/0194297 A1     Jul. 7, 2016

(30) Foreign Application Priority Data
Aug. 14, 2013 (EP) .................................. 13180425

(51) Int. Cl.
| C08G 59/04 | (2006.01) |
| C07D 303/18 | (2006.01) |
| C07C 31/133 | (2006.01) |
| C07C 31/27 | (2006.01) |
| C08G 59/24 | (2006.01) |
| C08G 59/50 | (2006.01) |

(52) U.S. Cl.
CPC .......... *C07D 303/18* (2013.01); *C07C 31/133* (2013.01); *C07C 31/276* (2013.01); *C08G 59/04* (2013.01); *C08G 59/24* (2013.01); *C08G 59/50* (2013.01)

(58) Field of Classification Search
CPC ....................................................... C08G 59/04
USPC .......................................................... 528/408
See application file for complete search history.

(56) References Cited

U.S. PATENT DOCUMENTS

| 4,948,700 A | 8/1990 | Maeda et al. |
| 2004/0147638 A1 | 7/2004 | Kim et al. |
| 2012/0116048 A1 | 5/2012 | Evans et al. |

FOREIGN PATENT DOCUMENTS

| DE | 32 28 719 A1 | 2/1984 |
| JP | 7-150013 A | 6/1995 |
| WO | WO 2010/100122 A1 | 9/2010 |
| WO | WO 2012/089657 A2 | 7/2012 |
| WO | WO 2012/091701 A1 | 7/2012 |

OTHER PUBLICATIONS

International Search Report issued Aug. 26, 2014 in PCT Application No. PCT/EP2014/066327.

Ha Q. Pham et al. "Epoxy Resins", Ullmann's Encyclopedia of Industrial Chemistry, vol. 13, 2012, pp. 155-244.

*Primary Examiner* — Duc Truong
(74) *Attorney, Agent, or Firm* — Oblon, McClelland, Maier & Neustadt, L.L.P.

(57) ABSTRACT

Cured epoxy resins are widespread because of their excellent mechanical and chemical properties. Typically, epoxy resins based on bisphenol A diglycidyl ethers or bisphenol F diglycidyl ethers are used, but these are problematic for many sectors because of their effect on the endocrine system. The present invention relates to glycidyl ethers of limonene-based diols and/or polyols, and to curable epoxy resin compositions based thereon as alternatives to the bisphenol A diglycidyl ethers or bisphenol F diglycidyl ethers, or the epoxy resin compositions based thereon.

15 Claims, No Drawings

GLYCIDYL ETHERS OF LIMONENE DERIVATIVES AND OLIGOMERS THEREOF AS CURABLE EPOXY RESINS

The present invention relates to glycidyl ethers of the formula I, which are glycidyl ethers of limonene derivatives of the formula II having two or more glycidyl groups. The invention further relates to oligomers of the glycidyl ethers of the formula I. The invention also relates to processes for preparing these monomeric and oligomeric glycidyl ethers, and to the use thereof for production of adhesives, composites, moldings or coatings. The present invention further relates to a curable epoxy resin composition comprising a curing agent component and a resin component which comprises, as a polyepoxide compound, at least one glycidyl ether of the formula I, an oligomer of a glycidyl ether of the formula I or an oligomer based on a glycidyl ether of the formula I. The invention further relates to a process for curing these curable epoxy resin compositions, and to cured epoxy resins obtainable or obtained by curing this curable epoxy resin composition. The invention also provides the limonene derivatives of the formula II having 3 or 4 hydroxyl groups used as an intermediate for the preparation of the glycidyl ethers of the invention.

Epoxy resins is a designation customary for oligomeric compounds having an average of more than one epoxide group per molecule, which are converted by reaction with suitable hardeners (curing agents) or by polymerization of the epoxide groups to thermosets, or cured epoxy resins. Cured epoxy resins, on account of their outstanding mechanical and chemical properties, such as high impact strength, high abrasion resistance, good heat and chemicals resistance, more particularly a high level of resistance toward alkalis, acids, oils and organic solvents, and high weathering resistance, excellent adhesiveness to a large number of materials, and high electrical insulation capacity, are widespread. They serve as a matrix for fiber composites and are often a major constituent in electrical laminates, structural adhesives, casting resins, coatings, and powder coating materials.

The majority of commercial (uncured) epoxy resins are prepared by coupling epichlorohydrin to compounds which possess at least two reactive hydrogen atoms, such as polyphenols, monoamines and diamines, aminophenols, heterocyclic imides and amides, aliphatic diols or polyols or dimeric fatty acids. Epoxy resins which derive from epichlorohydrin are referred to as glycidyl-based resins. Generally speaking, bisphenol A diglycidyl ether or bisphenol F diglycidyl ether, or the corresponding oligomers, are used as epoxy resins.

Exacting requirements are imposed especially on coatings of containers for the storage of foods and drinks. The coating accordingly is to resist strongly acidic or salty foods (e.g. tomatoes) or drinks, so that no corrosion occurs to the metal, which might in turn lead to contamination of the contents. Moreover, the coating must not impact the flavor or appearance of the foods. Since the production of the containers often involves further forming of containers that have already been coated, the coating must be flexible. Many contents, such as foods, are not pasteurized until they are in the can; the coating therefore, is required to withstand heating at 121° C. for at least 2 hours without damage and without migration of ingredients.

The use of epoxy resins based on bisphenol A or bisphenol F diglycidyl ethers is becoming identified as a problem in an increasing number of sectors, since the corresponding diols are seen as problematic on account of their effect on the endocrine system.

To solve this problem, a variety of proposals have been made:

US 2012/0116048 discloses a bisphenol A (BPA) and bisphenol F (BPF) free polymer, which as well as ester bonds also comprises hydroxyl ether bridges, with use being made of diepoxides which are based on open-chain aliphatic diols such as neopentyl glycol (NPG), on simple cycloaliphatic diols such as 1,4-cyclohexanedimethanol or on aromatic diols such as resorcinol. From experience, however, the aliphatic and cycloaliphatic diols described produce coatings which are very soft and have low temperature and chemicals resistance.

WO 2012/089657 discloses a BPA-free preparation comprising a film-forming resin and an adhesion promoter. The resin is an epoxidized resin prepared for example from the diglycidyl ethers of NPG, ethylene glycol, propylene or dipropylene glycol, 1,4-butanediol or 1,6-hexanediol. Here, the same restrictions on the properties of the coating are anticipated as in the previous example.

WO 2010/100122 proposes a coating system which is obtainable by reaction of an epoxidized vegetable oil with hydroxy-functional compounds, for example propylene glycol, propane-1,3-diol, ethylene glycol, NPG, trimethylolpropane, diethylene glycol, etc.

US 2004/0147638 describes a 2-layer (core/shell) system, wherein the core is formed from a BPA- or BPF-based epoxy resin, and the outer layer from, for example an acrylate resin. The critical issue here is whether the outer layer is truly able fully to prevent the migration of BPA or bisphenol A diglycidyl ether (BADGE) into the contents.

WO 2012/091701 proposes various diols and their diglycidyl ethers as a substitute for BPA or BADGE for epoxy resins, including derivatives of BPA and ring-hydrogenated BPA, alicyclic diols based on cyclobutane and diols having a furan ring as their parent structure.

The object on which the present invention is based is that of providing monomeric and/or oligomeric diglycidyl ether compounds for use in epoxy resin systems, especially as an at least partial substitute for BADGE in corresponding epoxy resin systems, particularly for use in the coating of containers.

The present invention relates accordingly to glycidyl ethers of the formula I

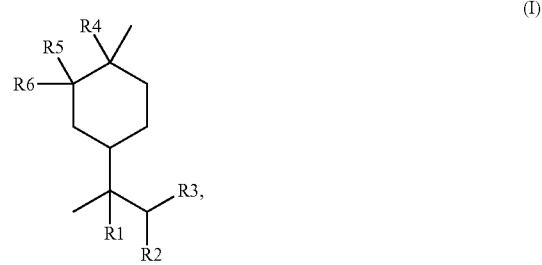

where
R1=H and R2=CH$_2$OA and R3=H, or
R1=H and R2=CH$_2$OA and R3=CR7R8OA, or
R1=CH$_2$OA and R2=H and R3=H,
and where
R4=H and R5=CH$_2$OA and R6=H, or
R4=H and R5=CH$_2$OA and R6=CR7R8OA, or R4=CH₂OA and R5=H and R6=H,
and where
A is a glycidyl group

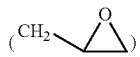

or a hydrogen atom, and
R7 and R8 are each independently a hydrogen atom or a C₁-C₄-alkyl group, preferably a hydrogen atom,
and where
at least 2 of, preferably all of, the A radicals are each a glycidyl group.

The glycidyl ethers of the formula I in this specification of the radicals are also referred to as "glycidyl ethers I" for short in the context of this invention.

In a particular embodiment, the present invention relates to glycidyl ethers of the formula I in the variant A,
where
R1=H and R2=CH₂OA and R3=H, or
R1=CH₂OA and R2=H and R3=H,
and where
R4=H and R5=CH₂OA and R6=H, or
R4=CH₂OA and R5=H and R6=H,
and where
A is a glycidyl group The glycidyl ethers of the formula I in this specification of the radicals (variant A) are also referred to as "glycidyl ethers IA" for short in the context of this invention.

In a particular embodiment, the present invention relates to glycidyl ethers of the formula I in the variant B,
where
R1=H and R2=CH₂OA and R3=H, or
R1=H and R2=CH₂OA and R3=CR7R8OA, or
R1=CH₂OA and R2=H and R3=H,
and where
R4=H and R5=CH₂OA and R6=H, or
R4=H and R5=CH₂OA and R6=CR7R8OA, or
R4=CH₂OA and R5=H and R6=H,
and where
A is a glycidyl group or a hydrogen atom, and
R7 and R8 are each independently a hydrogen atom or a C₁-C₄-alkyl group, preferably a hydrogen atom, and
R3 and R6 are not both simultaneously a hydrogen atom,
and where
at least 2 of, but preferably all of, the A radicals are each a glycidyl group.

The glycidyl ethers of the formula I in this specification of the radicals (variant B) are also referred to as "glycidyl ethers IB" for short in the context of this invention.

The glycidyl ethers IA and IB are subsets of the glycidyl ethers I.

The glycidyl ethers I, IA and IB explicitly encompass all the stereoisomers possible in each case.

A C₁-C₄-alkyl group is a methyl, ethyl, n-propyl, isopropyl, n-butyl, isobutyl, sec-butyl or tert-butyl group.

The term glycidyl ethers I, IA or IB also relates explicitly to individual specific compounds from the particular group, and also to mixtures of a plurality of specific compounds in the particular group.

The invention further provides oligomers of the glycidyl ethers I, IA or IB too, which form through the intermolecular reaction of glycidylated radicals with non-glycidylated radicals having hydroxyl groups in the glycidyl ethers I, IA or IB, and the partially glycidylated (having 1 glycidyl group) or non-glycidylated (not having any glycidyl group) derivatives thereof with opening of the oxirane ring, where the hydroxyl group which forms through the ring-opening of the oxirane ring in the oligomer may in turn also be in glycidylated form. The oligomers have 2 to 100 and preferably 2 to 30 monomeric units (oligomerization level). They may be linear or branched, and are preferably linear. They have an average of at least 1.3, preferably at least 1.5 and more preferably at least 2 glycidyl groups. The term oligomer of the glycidyl ethers I, IA or IB also encompasses mixtures of various oligomers (for example oligomers having different oligomerization levels, having different branching structures or composed of different monomers of the respective variant (glycidyl ethers I, IA or IB)). These oligomers are also referred to in the context of this invention as oligomeric glycidyl ethers I, IA or IB.

The invention thus provides a glycidyl ether selected from the group consisting of glycidyl ethers I and oligomeric glycidyl ethers thereof (oligomeric glycidyl ethers I), where the oligomeric glycidyl ether forms through the intermolecular reaction of glycidylated radicals with non-glycidylated radicals comprising hydroxyl groups in the monomeric glycidyl ether of the formula I and the partially glycidylated or non-glycidylated derivatives thereof with opening of the oxirane ring, where the hydroxyl group which forms through the ring-opening of the oxirane ring in the oligomeric glycidyl ether may in turn also be in glycidylated form, and where the oligomeric glycidyl ether has an oligomerization level of 2 to 100 and an average of at least 1.3 glycidyl groups.

The invention thus also provides a glycidyl ether selected from the group consisting of glycidyl ethers IA and oligomeric glycidyl ethers thereof (oligomeric glycidyl ethers IA), where the oligomeric glycidyl ether forms through the intermolecular reaction of glycidylated radicals with non-glycidylated radicals comprising hydroxyl groups in the monomeric glycidyl ether of the formula I and the partially glycidylated or non-glycidylated derivatives thereof with opening of the oxirane ring, where the hydroxyl group which forms through the ring-opening of the oxirane ring in the oligomeric glycidyl ether may in turn also be in glycidylated form, and where the oligomeric glycidyl ether has an oligomerization level of 2 to 100 and an average of at least 1.3 glycidyl groups.

The invention likewise provides a glycidyl ether selected from the group consisting of glycidyl ethers IB and oligomeric glycidyl ethers thereof (oligomeric glycidyl ethers IB), where the oligomeric glycidyl ether forms through the intermolecular reaction of glycidylated radicals with non-glycidylated radicals comprising hydroxyl groups in the monomeric glycidyl ether of the formula I and the partially glycidylated or non-glycidylated derivatives thereof with opening of the oxirane ring, where the hydroxyl group which forms through the ring-opening of the oxirane ring in the oligomeric glycidyl ether may in turn also be in glycidylated form, and where the oligomeric glycidyl ether has an oligomerization level of 2 to 100 and an average of at least 1.3 glycidyl groups.

One embodiment of the invention relates to mixtures of monomeric glycidyl ethers I, IA, or IB and the corresponding oligomeric glycidyl ether I, IA, or IB.

The present invention further relates to a process for preparing monomeric and oligomeric glycidyl ethers I, IA or IB, comprising the reaction of the corresponding limonene derivatives II, IIA or IIB with epichlorohydrin.

These limonene derivatives II are limonene derivatives of the formula II

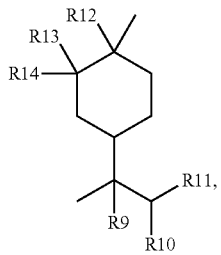

(II)

where
R9=H and R10=CH$_2$OH and R11=H, or
R9=H and R10=CH$_2$OH and R11=CR7R8OH, or
R9=CH$_2$OH and R10=H and R11=H,
and where
R12=H and R13=CH$_2$OH and R14=H, or
R12=H and R13=CH$_2$OH and R14=CR7R8OH, or
R12=CH$_2$OH and R13=H and R14=H,
and where
R7 and R8 are each independently a hydrogen atom or a C$_1$-C$_4$-alkyl group, preferably a hydrogen atom.

The limonene derivatives IIA are limonene derivatives of the formula II in variant A with the following specification of the radicals:
R9=H and R10=CH$_2$OH and R11=H, or
R9=CH$_2$OH and R10=H and R11=H,
and
R12=H and R13=CH$_2$OH and R14=H, or
R12=CH$_2$OH and R13=H and R14=H,
The limonene derivatives IIA are diols.

The limonene derivatives IIB are limonene derivatives of the formula II in variant B with the following specification of the radicals:
R9=H and R10=CH$_2$OH and R11=H, or
R9=H and R10=CH$_2$OH and R11=CR7R8OH, or
R9=CH$_2$OH and R10=H and R11=H,
and
R12=H and R13=CH$_2$OH and R14=H, or
R12=H and R13=CH$_2$OH and R14=CR7R8OH, or
R12=CH$_2$OH and R13=H and R14=H,
where
R7 and R8 are each independently a hydrogen atom or a C$_1$-C$_4$-alkyl group, preferably a hydrogen atom, and
R11 and R14 are not both a hydrogen atom at the same time.

The limonene derivatives IIB are tri- and tetrahydric alcohols (polyols).

The glycidylation reaction generally gives rise to a mixture of monomeric and oligomeric glycidyl ethers. The monomeric glycidyl ethers can be separated from the oligomeric glycidyl ethers by means of separation methods known to those skilled in the art, for example chromatographic, extractive or distillative processes.

Preferably, the inventive conversion of the limonene derivatives II, IIA or IIB to the corresponding glycidyl ethers is effected with 1 to 20 and preferably with 1 to 10 equivalents of epichlorohydrin at a temperature within a range from 20 to 180° C., preferably from 70 to 150° C., in the presence of a Lewis acid as a catalyst, preferably in the presence of tin(IV) chloride. Subsequently, the reaction mixture is admixed with a base (for example dilute sodium hydroxide solution) and heated (for example under reflux) for a further period of time (for example 1 to 5 h). Thereafter, the product can be isolated by means of phase separation and wash steps with water.

In an alternative variant, 1 to 20 equivalents, preferably 2 to 10 equivalents, of epichlorohydrin are used for the preparation of the inventive glycidyl ethers. The reaction is effected typically within a temperature range from −10° C. to 120° C., preferably 20° C. to 60° C. To accelerate the conversion, it is possible to add bases such as aqueous or alcoholic solutions or dispersions of inorganic salts, for example LiOH, NaOH, KOH, Ca(OH)$_2$ or Ba(OH)$_2$. In addition, it is possible to use suitable catalysts such as tertiary amines.

The limonene derivatives IIA or IIB can be prepared according to the reaction scheme which follows from limonene. For this purpose, in a first step, limonene is converted by means of hydroformylation (HF) with carbon monoxide (CO) and hydrogen (H2) to the corresponding dicarbonyl compounds. These can be hydrogenated (Hyd) either directly to the diols (limonene derivatives IIA) or, after an aldol reaction (AD) with, for example, formaldehyde (H2CO), to the polyols (limonene derivatives IIB), for example with hydrogen (H2). The aldol reaction is only possible when a hydrogen atom is bonded to the alpha-carbon atom to the carbonyl group. The limonene derivatives II correspond to the entirety of the group of limonene derivatives IIA and IIB. Limonene derivatives IIA and the preparation thereof are also described in DE 3228719 A1.

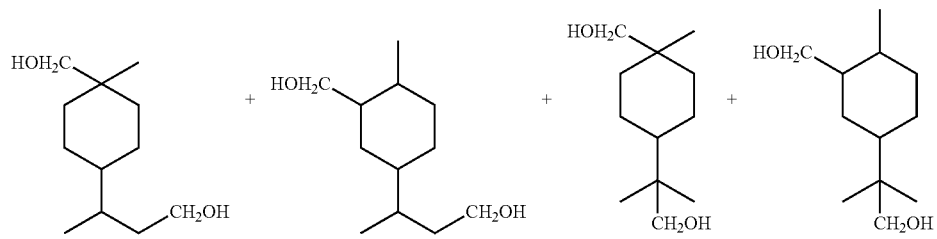

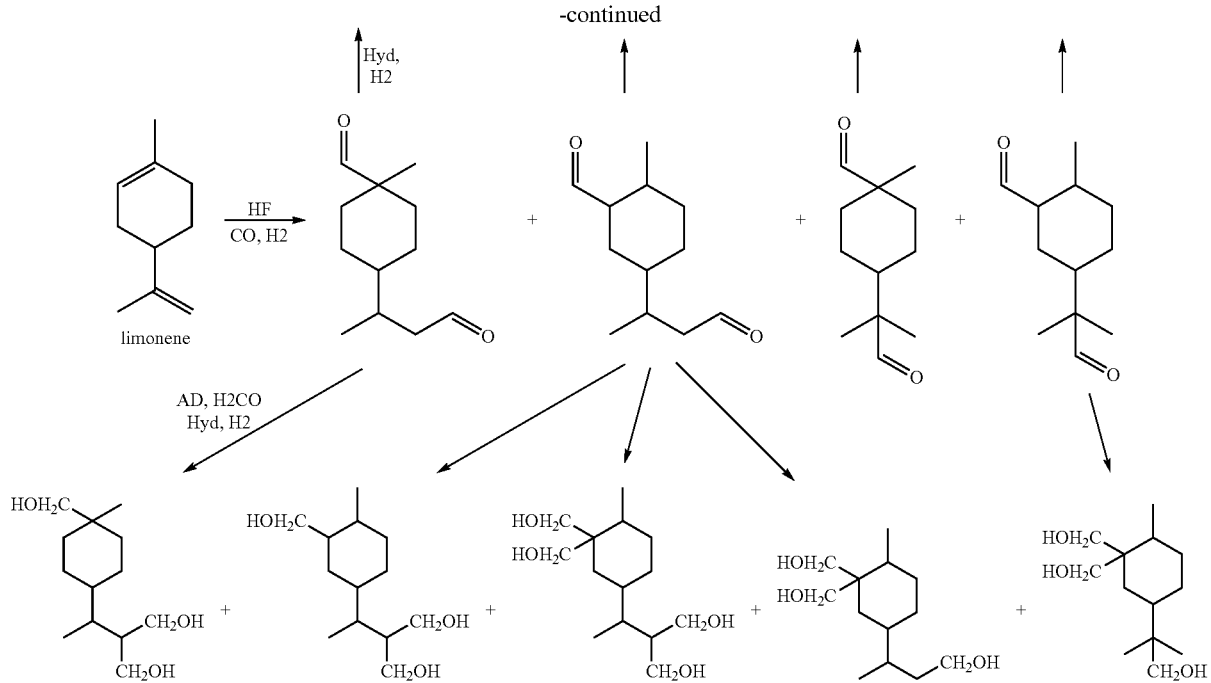

The conversion of the limonene to the corresponding dialdehydes is typically effected by means of hydroformylation. This involves converting the limonene with a mixture of carbon monoxide and hydrogen (synthesis gas) in the presence of a hydroformylation catalyst (for example organometallic cobalt or rhodium compounds) at elevated pressure (for example 10 to 100 bar gauge) and at temperatures in the range from, for example, 40 to 200° C. to give the corresponding dialdehydes.

The dialdehyde derivatives of the limonene can be hydrogenated directly to the corresponding diols (limonene derivatives IIA). Such a hydrogenation can be effected, for example, by means of hydrogen under elevated pressure in the presence of a hydrogenation catalyst.

Alternatively, the dialdehyde derivatives of the limonene can also be converted to the corresponding polyols (limonene derivatives IIB). For this purpose, the dialdehyde derivatives of the limonene, if they have a hydrogen atom in the alpha position to the aldehyde group (C,H-acidic compound), are converted first by aldol reaction with a carbonyl compound of the formula R7R8C=O, preferably with formaldehyde (R7=H and R8=H), forming a new C—C bond, to give the beta-hydroxy aldehyde. Subsequently, the aldehyde groups can be reduced as described above for the dialdehyde derivatives of limonene.

The invention thus provides a process for preparing glycidyl ethers IA, comprising (i) the hydroformylation of limonene with a mixture of carbon monoxide and hydrogen in the presence of a hydroformylation catalyst at elevated pressure to give the corresponding dialdehydes, and (ii) the catalytic hydrogenation of the dialdehydes from the hydroformylation to give the corresponding diols, and (iii) the reaction of the diols from the catalytic hydrogenation with epichlorohydrin to give the corresponding glycidyl ethers IA.

The invention thus provides also a process for preparing glycidyl ethers IB, comprising (i) the hydroformylation of limonene with a mixture of carbon monoxide and hydrogen in the presence of a hydroformylation catalyst at elevated pressure to give the corresponding dialdehydes, and (ii) the aldol reaction of the dialdehydes from the hydroformylation with a carbonyl compound of the formula R7R8C=O with formation of a new C—C bond to give the corresponding beta-hydroxy aldehydes, (iii) the catalytic hydrogenation of the beta-hydroxy aldehydes from the aldol reaction to give the corresponding tri- and tetrahydric alcohols, and (iv) the reaction of the tri- and tetrahydric alcohols from the catalytic hydrogenation with epichlorohydrin to give the corresponding glycidyl ethers IB.

The invention also provides the limonene derivatives IIB, which serve as intermediates in the preparation of the inventive glycidyl ethers IB.

The present invention further relates to processes for preparing oligomers based on glycidyl ethers I, IA or IB, by reaction of monomeric glycidyl ethers I, IA or IB with diols (chain extension). For this purpose, monomeric glycidyl ether I, IA or IB, or a mixture of monomeric glycidyl ethers I, IA or IB and corresponding oligomeric glycidyl ethers I, IA or IB, is reacted with one or more diols. In this case, the oligomeric glycidyl ether I, IA or IB preferably has a low oligomerization level, especially an oligomerization level of 5 to 10. For this purpose, preferably 0.01 to 0.95, more preferably 0.05 to 0.8 and especially 0.1 to 0.4 equivalent of the diol is used, based on the glycidyl ether(s) used. Preferably, the result of a substoichiometric use of the diol(s) is that the resulting oligomer based on glycidyl ethers I, IA or IB has an average of more than 1, preferably more than 1.5, more preferably more than 1.9, epoxy groups per molecule. The reaction is effected typically within a temperature range from 50° C. to 200° C., preferably from 60° C. to 160° C. Suitable diols are typically aromatic, cycloaliphatic or aliphatic dihydroxyl compounds, for example furandimethanol, ring-hydrogenated bisphenol A, ring-hydrogenated bisphenol F, neopentyl glycol, bisphenol A, bisphenol F or bisphenol S, preferably furandimethanol, ring-hydrogenated bisphenol A or ring-hydrogenated bisphenol F.

Accordingly, the present invention also provides oligomers based on glycidyl ethers I, IA or IB, which are obtainable or obtained by reacting a monomeric glycidyl ether I, IA or IB or the corresponding oligomeric glycidyl ether or a mixture of monomeric glycidyl ether I, IA or IB and the corresponding oligomeric glycidyl ether with one or more diols. Preferably, this oligomeric glycidyl ether I, IA or IB has a low oligomerization level, especially an oligomerization level of 5 to 10. In a particular embodiment, the one or more diol(s) used is/are not identical to the limonene derivatives IIA, as a result of which mixed oligomers based on glycidyl ethers I, IA or IB are obtainable or are obtained. In a particular embodiment, the one or more diols used are identical to the limonene derivatives IIA, as a result of which oligomers based on glycidyl ethers I, IA or IB are obtainable or are obtained. In an analogous manner, it is also possible to selectively prepare higher molecular weight oligomeric glycidyl ethers I, IA or IB proceeding from oligomeric glycidyl ethers I, IA or IB having a low oligomerization level.

The present invention also relates to curable epoxy resin compositions comprising a curing agent component comprising at least one curing agent, and a resin component comprising at least one polyepoxide compound selected from the group consisting of monomeric glycidyl ethers I, IA or IB, oligomeric glycidyl ethers I, IA or IB and oligomer based on glycidyl ethers I, IA or IB.

The present invention also relates to a curable epoxy resin composition comprising a curing agent component comprising at least one curing agent, and a resin component comprising at least one polyepoxide compound selected from the group consisting of monomeric glycidyl ethers I, IA or IB, oligomeric glycidyl ethers I, IA or IB and mixed oligomer based on glycidyl ethers I, IA or IB.

Preferably, the present invention relates to curable epoxy resin compositions comprising a curing agent component comprising at least one curing agent, and a resin component comprising at least one polyepoxide compound selected from the group consisting of monomeric glycidyl ethers I and oligomeric glycidyl ethers I. More particularly, the present invention relates to curable epoxy resin compositions comprising a curing agent component comprising at least one curing agent, and a resin component comprising at least one polyepoxide compound selected from the group consisting of monomeric glycidyl ethers IA, monomeric glycidyl ethers IB, oligomeric glycidyl ethers IA and oligomeric glycidyl ethers IB.

In a particular embodiment, the present invention relates to curable epoxy resin compositions comprising a curing agent component comprising at least one curing agent, and a resin component comprising at least one polyepoxide compound selected from the group consisting of oligomeric glycidyl ethers IA and oligomeric glycidyl ethers IB, where the epoxy equivalent weight (EEW) of the oligomeric glycidyl ethers used, on statistical average, is between 130 and 6000 g/mol, especially between 140 and 1000 g/mol.

The curable epoxy resin composition of the invention comprises preferably less than 40% by weight, more preferably less than 10% by weight, especially preferably less than 5% by weight, in particular less than 1% by weight, of bisphenol A or F based compounds, based on the overall resin component. The curable epoxy resin composition of the invention is preferably free from bisphenol A or F based compounds. Bisphenol A or F based compounds in the context of the present invention are bisphenol A and F themselves, their diglycidyl ethers, and also oligomers or polymers based thereon.

In a preferred embodiment of the curable epoxy resin composition of the invention, the inventive polyepoxide compounds make up a total proportion of at least 40% by weight, preferably at least 60% by weight, more particularly at least 80% by weight, based on the overall resin component.

In a preferred embodiment of the curable epoxy resin composition of the invention, the overall resin component makes up at least 10% by weight, more particularly at least 25% by weight, based on the overall curable epoxy resin composition.

In the context of the present invention, all epoxide compounds and only the epoxide compounds of the curable epoxy resin composition are to be assigned to the resin component. Epoxide compounds in the context of the present invention are compounds having at least one epoxide group—hence including, for example, corresponding reactive diluents.

The epoxide compounds of the resin component preferably have, on statistical average, at least 1.1, more preferably at least 1.5 and more particularly at least 1.9 epoxide groups per molecule.

Curing agents for the purposes of the invention are compounds suitable for producing crosslinking of the polyepoxide compounds of the invention.

Reaction with curing agents can be used to convert polyepoxide compounds to nonfusible, three-dimensionally "crosslinked", thermoset materials.

In the curing of epoxy resins, a distinction is made between two types of curing. In the first case, the curing agent has at least two functional groups which are able to react with the oxirane groups and/or hydroxyl groups of the polyepoxide compounds, with formation of covalent bonds (polyaddition reaction). In the course of curing, a polymeric network is then formed, made up of units which originate from the polyepoxide compounds and units originating from the curing agent molecules, these units being linked covalently to one another, and the degree of crosslinking being controllable via the relative amounts of the functional groups in the curing agent and in the polyepoxide compound. In the second case a compound is used which brings about the homopolymerization of polyepoxide compounds with one another. Such a compound is often also termed an initiator or catalyst. Homopolymerization inducing catalysts are Lewis bases (anionic homopolymerization; anionically curing catalysts) or Lewis acids (cationic homopolymerization; cationically curing catalysts). They bring about the formation of ether bridges between the epoxide compounds. It is assumed that the catalyst reacts with a first epoxide group, accompanied by ring opening, to form a reactive hydroxyl group, which reacts in turn with a further epoxide group to form an ether bridge, so leading to a new reactive hydroxyl group. On account of this reaction mechanism, the substoichiometric use of such catalysts is sufficient for curing. Imidazole is an example of a catalyst which induces the anionic homopolymerization of epoxide compounds. Boron trifluoride is an example of a catalyst which triggers a cationic homopolymerization. Additionally, mixtures of different curing agents which enter into a polyaddition reaction, and mixtures of curing agents which induce homopolymerization, and also mixtures of curing agents which undergo polyaddition reaction and curing agents which induce homopolymerization, can be used for the curing of polyepoxide compounds.

Suitable functional groups which are able to enter into a polyaddition reaction with the oxirane groups of polyepoxide compounds (epoxy resins) are, for example, amino groups, hydroxyl groups, thioalcohols and derivatives thereof, isocyanates, and carboxyl groups and/or derivatives thereof, such as anhydrides. Accordingly, curing agents used for epoxy resins typically include aliphatic, cycloaliphatic and aromatic polyamines, carboxylic anhydrides, polyamidoamines, amino resins, for example formaldehyde condensation products of melamine, urea, benzoguanamine or phenolic resins such as novolaks, for example. Oligomeric or polymeric, acrylate-based curing agents with hydroxy functions or glycidyl functions in the side chain, and also epoxyvinyl ester resins, are also used. The skilled person is aware of those applications for which a fast- or slow-acting curing agent is used. For example, for storage-stable one-component formulations, he or she will use a curing agent which is very slow-acting (or which acts only at a relatively high temperature). Optionally, a curing agent will be used which is liberated as an active form only under application conditions, examples being ketimines or aldimines. Known curing agents possess a linear or no more than slightly crosslinked structure. They are described, for example in Ullmann's Encyclopedia of Industrial Chemistry, 5th edition on CD-ROM, 1997, Wiley-VCH, chapter "Epoxy Resins", hereby incorporated in full by reference.

Examples of suitable curing agents for the curable epoxy resin composition of the invention include polyphenols, polycarboxylic acids, polymercaptans, polyamines, primary monoamines, sulfonamides, aminophenols, aminocarboxylic acids, carboxylic anhydrides, carboxylic acids containing phenolic hydroxyl groups, sulfanilamides, and also mixtures thereof. In the context of this invention, the respective poly compounds (e.g. polyamine) also include the corresponding di compounds (e.g. diamine).

Preferred curing agents for the curable epoxy resin composition of the invention are amino curing agents and phenolic resins.

In one particular embodiment the curable epoxy resin composition of the invention comprises an amino curing agent as curing agent. Amino curing agents suitable for the polyaddition reaction are compounds which possess at least two secondary or at least one primary amino group(s). The linking of the amino groups of the amino curing agent with the epoxide groups of the polyepoxide compound forms polymers whose units originate from the amino curing agents and from the polyepoxide compounds. Amino curing agents are therefore used generally in a stoichiometric ratio to the epoxide compounds. If, for example, the amino curing agent has two primary amino groups, and can therefore be coupled with up to four epoxide groups, crosslinked structures may be formed.

The amino curing agents of the curable epoxy resin composition of the invention possess at least one primary amino group or two secondary amino groups. Starting from polyepoxide compounds having at least two epoxide groups, curing can be accomplished by a polyaddition reaction (chain extension) using an amino compound having at least two amino functions. The functionality of an amino compound here corresponds to its number of NH bonds. A primary amino group therefore has a functionality of 2, while a secondary amino group has a functionality of 1. The linking of the amino groups of the amino curing agent with the epoxide groups of the polyepoxide compound produces polymers from the amino curing agent and the polyepoxide compound, the epoxide groups being reacted to form free OH groups. It is preferred to use amino curing agents having a functionality of at least 3 (for example, at least 3 secondary amino groups or at least one primary and one secondary amino group), more particularly those having two primary amino groups (functionality of 4).

Preferred amino curing agents are Dimethyl Dicykan (DMDC), dicyandiamide (DICY), isophoronediamine (IPDA), diethylenetriamine (DETA), triethylenetetramine (TETA), bis(p-aminocyclohexyl)methane (PACM), methylenedianiline (e.g. 4,4'-methylenedianiline), polyetheramines, e.g. polyetheramine D230, diaminodiphenylmethane (DDM), diaminodiphenylsulfone (DDS), 2,4-toluenediamine, 2,6-toluenediamine, 2,4-diamino-1-methylcyclohexane, 2,6-diamino-1-methylcyclohexane, 2,4-diamino-3,5-diethyltoluene, 2,6-diamino-3,5-diethyltoluene, 1,2-diaminobenzene, 1,3-diaminobenzene, 1,4-diaminobenzene, diaminodiphenyl oxide, 3,3',5,5'-tetramethyl-4,4'-diaminodiphenyl and 3,3'-dimethyl-4,4'-diaminodiphenyl, and also aminoplast resins, for example condensation products of aldehydes such as formaldehyde, acetaldehyde, crotonaldehyde or benzaldehyde with melamine, urea or benzoguanamine, and also mixtures thereof. Particularly preferred amino curing agents for the curable composition of the invention are Dimethyl Dicykan (DMDC), dicyandiamide (DICY), isophoronediamine (IPDA) and methylenedianiline (e.g. 4,4'-methylenedianiline) and also aminoplast resins, for example condensation products of aldehydes such as formaldehyde, acetaldehyde, crotonaldehyde or benzaldehyde with melamine, urea or benzoguanamine.

In the context of the curable epoxy resin composition of the invention, polyepoxide compound and amino curing agent are preferably used in an approximately stoichiometric ratio in terms of the epoxide and amino functionalities. Particularly suitable ratios of epoxide groups to amino functionality are, for example, 1:0.8 to 0.8:1.

In one particular embodiment the curable epoxy resin composition of the invention comprises a phenolic resin as curing agent. Phenolic resins suitable for the polyaddition reaction possess at least two hydroxyl groups. Linking of the hydroxyl groups of the phenolic resin with the epoxide groups of the polyepoxide compound forms polymers whose units originate from phenolic resins and from the polyepoxide compounds. Phenolic resins can generally be used both in a stoichiometric ratio and in a substoichiometric ratio to the epoxide compounds. When substoichiometric amounts of the phenolic resin are used the reaction of the secondary hydroxyl groups of the existing epoxy resin with epoxide groups is promoted by the use of suitable catalysts.

Examples of suitable phenolic resins are novolaks, phenolic resoles, condensation products of aldehydes (preferably formaldehyde and acetaldehyde) with phenols in general. Preferred phenols are phenol, cresol, xylenols, p-phenylphenol, p-tert-butylphenol, p-tert-amylphenol, cyclopentylphenol, and p-nonyl- and p-octylphenol.

The curable epoxy resin composition of the invention may also comprise an accelerator for the curing. Suitable curing accelerators are, for example, imidazole or imidazole derivatives or urea derivatives (urons), for example 1,1-dimethyl-3-phenylurea (fenuron). The use of tertiary amines, for example triethanolamine, benzyldimethylamine, 2,4,6-tris(dimethylaminomethyl)-phenol and tetramethylguanidine as curing accelerators has also been described (U.S. Pat. No. 4,948,700). It is known, for example, that the curing of epoxy resins with DICY can be accelerated by addition of fenuron.

The curable epoxy resin composition of the invention may also comprise a diluent.

Diluents for the purposes of this invention are conventional diluents or reactive diluents. The addition of diluent to a curable epoxy resin composition typically lowers its viscosity.

Conventional diluents are, customarily, organic solvents or mixtures thereof, examples being ketones such as acetone, methyl ethyl ketone, methyl isobutyl ketone (MIBK), diethyl ketone or cyclohexanone, esters of aliphatic carboxylic acids such as ethyl acetate, propyl acetate, methoxypropyl acetate or butyl acetate, glycols such as ethylene glycol, diethylene glycol, triethylene glycol or propylene glycol etc., glycol derivatives such as ethoxyethanol, ethoxyethanol acetate, ethylene or propylene glycol monomethyl or dimethyl ethers, aromatic hydrocarbons such as toluene or xylenes, aliphatic hydrocarbons such as heptane, for example, and also alkanols such as methanol, ethanol, n- or isopropanol or butanols. In the course of the curing of the epoxy resin, they evaporate from the resin composition. This can lead to an unwanted reduction in resin volume (contraction) or to the formation of pores, and so may adversely affect mechanical properties of the cured material, for example the fracture resistance, or even the surface properties.

Reactive diluents are substances of low molecular mass which, in contrast to conventional solvents, have functional groups, generally oxirane groups, which are able to react with the hydroxyl groups of the resin and/or with the functional groups of the curing agent, with formation of covalent bonds. Reactive diluents in the sense of the present invention are aliphatic or cycloaliphatic compounds. They do not evaporate in the course of curing, but instead are bound covalently, in the course of curing, into the resin matrix as it forms. Examples of suitable reactive diluents are mono- or polyfunctional oxiranes. Examples of monofunctional reactive diluents are glycidyl ethers of aliphatic and cycloaliphatic monohydroxyl compounds having in general 2 to 20 carbon atoms, for example ethylhexyl glycidyl ether and also glycidyl esters of aliphatic or cycloaliphatic monocarboxylic acids having generally 2 to 20 carbon atoms. Examples of polyfunctional reactive diluents are, in particular, glycidyl ethers of polyfunctional alcohols having in general 2 to 20 carbon atoms, and containing on average typically 1.5 to 4 glycidyl groups, such as 1,4-butanediol diglycidyl ether, 1,6-hexanediol diglycidyl ether, diethylene glycol diglycidyl ether or the glycidyl ethers of trimethylolpropane or of pentaerythritol. Reactive diluents described to date do enhance the viscosity properties of the epoxy resin compositions, but in many cases they impair the hardness of the cured resin and result in a relatively low solvent resistance. It is also known that the reactive diluents lower the reactivity of the epoxy resin compositions formulated with them, resulting in longer cure times.

The curable epoxy resin composition of the invention may also include fillers, such as pigments. Suitable fillers are metal oxides such as titanium dioxide, zinc oxide and iron oxide, or hydroxides, sulfates, carbonates, and silicates of these or other metals, examples being calcium carbonate, aluminum oxide, and aluminum silicates. Further suitable fillers are, for example, silicon dioxide, fumed or precipitated silica, and also carbon black, talc, barite or other non-toxic pigments. Mixtures of the fillers can be used as well. The weight fraction of the fillers in the coating, and their particle size and particulate hardness, and also their aspect ratio, will be selected by a skilled person in accordance with the requirements of the application.

The curable epoxy resin composition of the invention may comprise further additives according to the requirements, examples being defoamers, dispersants, wetting agents, emulsifiers, thickeners, biocides, cosolvents, bases, corrosion inhibitors, flame retardants, release agents and/or waxes.

The curable epoxy resin composition of the invention may also comprise reinforcing fibers such as glass fibers or carbon fibers. These fibers may take the form, for example, of short fiber pieces of a few mm to cm in length, or else continuous fibers, fiber windings or woven fiber fabrics.

The present invention further relates to a process for preparing a cured epoxy resin, comprising the curing of the curable epoxy resin composition.

The curing may take place under atmospheric pressure and at temperatures of less than 250° C., more particularly at temperatures less than 235° C., preferably at temperatures less than 220° C., more particularly in a temperature range from 40° C. to 220° C.

Curing of the curable epoxy resin composition to moldings takes place typically in a mold until dimensional stability has been achieved and the workpiece can be removed from the mold. The subsequent operation for removing inherent stresses in the workpiece and/or for completing the crosslinking of the curable epoxy resin is called heat-conditioning. In principle it is also possible to carry out the heat-conditioning process before the workpiece is removed from the mold, for the purpose of completing the crosslinking, for instance. The heat-conditioning operation typically takes place at temperatures at the limit of dimensional stiffness (Menges et al., "Werkstoffkunde Kunststoffe" (2002), Hanser-Verlag, 5th edition, p. 136). Heat-conditioning takes place typically at temperatures from 120° C. to 220° C., preferably at temperatures from 150° C. to 220° C. The cured workpiece is exposed to the heat-conditioning conditions typically for a time period of 30 to 240 minutes. Longer heat-conditioning times may also be appropriate, depending on the dimensions of the workpiece.

In the curing of the curable epoxy resin composition to form coatings, the substrate to be coated is first of all treated with the curable epoxy resin composition, after which the curable epoxy resin composition on the substrate is cured.

The treatment of the curable epoxy resin composition may take place before or after the shaping of the desired article, by dipping, spraying, roller application, spread application, knife coating, or the like, in the case of liquid formulations, or by application of a powder coating material. Application may take place to individual pieces (e.g., can parts) or to fundamentally continuous substrates, such as to strip rolls of steel in the case of coil coating, for example. Suitable substrates are typically those of steel, tinplate (galvanized steel) or aluminum (for beverage cans, for example). Curing of the curable epoxy resin composition following application to the substrate takes place typically in the temperature range from 20° C. to 250° C., preferably from 50° C. to 220° C., more preferably from 100° C. to 220° C. The time is typically 0.1 to 60 min, preferably 0.5 to 20 min, more preferably 1 to 10 min.

A comprehensive description of the common types of metal packaging and their production, metals and alloys used, and coating techniques is given in P. K. T. Oldring and U. Nehring: Packaging Materials, 7th Metal Packaging for Foodstuffs, ILSI Report, 2007, hereby incorporated by reference.

The present invention further relates to the cured epoxy resins obtained or obtainable by curing the curable epoxy resin composition of the invention, more particularly in the form of coatings on metallic substrates.

The present invention further relates to the use of monomeric or oligomeric glycidyl ethers I, IA or IB of the invention, or of oligomers based on glycidyl ethers I, IA or IB, or of the curable epoxy resin composition of the invention, for production of adhesives, composites, moldings and coatings, especially of coatings, preferably on containers, more particularly on containers for the storage of food.

The invention is illustrated in detail by the nonlimiting examples which follow.

Example 1

Preparation of Limonene Derivatives IIA

Limonene can, for example after being admixed with an alcoholic solvent and an Rh-containing hydroformylation catalyst, be converted to the corresponding dialdehydes in a stirred autoclave at an elevated temperature of, for example, 70 to 150° C. and with injection of synthesis gas ($CO/H_2$ (1:1)) up to a reaction pressure of, for example, 150 to 300 bar. The reaction mixture thus obtained, comprising the corresponding dialdehydes, after decompression to standard pressure and addition of distilled water and a hydrogenation catalyst, for example Raney nickel, and after injection of hydrogen to a reaction pressure of, for example, 50 to 200 bar, can be hydrogenated at an elevated temperature of, for example, 70 to 150° C. in a stirred autoclave. The reaction mixture thus obtained, comprising the corresponding diols, after decompression to standard pressure, can subsequently be freed of the hydrogenation catalyst by means of filtration and of the solvent by means of distillative removal, and then fractionally distilled for purification, in order to obtain the limonene derivative IIA, which is a mixture of the various diols.

Example 2

Preparation of Divinylbenzene Derivative IIB

Limonene derivative IIB can be prepared from limonene according to example 1, except that the reaction mixture from the reaction with synthesis gas (hydroformylation product), which comprises the corresponding aldehydes, is first subjected to an aldol reaction with formaldehyde, for example, prior to the performance of the hydrogenation step. For this purpose, the dialdehyde-containing reaction mixture from the hydroformylation reaction can be, optionally after preceding distillative purification, for example with a molar excess of aqueous formaldehyde (36.5%), and then a catalytic amount of triethanolamine is gradually metered into this reaction mixture, and it is subsequently neutralized with formic acid (98%) on completion of the aldol reaction. The reaction mixture thus prepared can, optionally after distillative purification, be subjected to a hydrogenation as described in example 1, such that divinylbenzene derivative IIB, which is a mixture of the various polyols, is obtainable.

Example 3

Preparation of Monomeric and/or Oligomeric Glycidyl Ethers IA

Limonene derivative IIA (0.7 mol, 136 g, according to ex. 1), which is, for example, a mixture of the various diols that would arise from the hydroformylation and subsequent hydrogenation of limonene, can be heated to 90° C. and admixed with tin(IV) chloride (7.6 mmol, 2 g). Subsequently, epichlorohydrin (1.4 mol, 129.5 g) can be added dropwise in portions, in the course of which the temperature was not supposed to rise, for example, above 140° C. or fall below 85° C. After the addition has ended, stirring, for example, at 90° C. can be continued until no epoxide content was measurable any longer. After cooling to room temperature, the reaction mixture can be admixed, for example, with 25% sodium hydroxide solution (1.4 mol, 224 g) and brought once to boiling. For workup, the product can be washed with water.

The monomeric glycidyl ether IA can be freed from the oligomers by distillation.

Example 4

Preparation of Monomeric and/or Oligomeric Glycidyl Ethers IB

Proceeding from the limonene derivative IIB (according to ex. 2), the glycidyl ether IB can be prepared analogously to example 3 by reaction with epichlorohydrin. In this case, the molar amount of epichlorohydrin used, based on the number of hydroxyl groups in the limonene derivative IIB, is preferably adjusted in comparison to the limonene derivative IIA.

The monomeric glycidyl ethers IB can be freed of the oligomers by distillative purification.

Example 5

Preparation of Cured Epoxy Resin from Monomeric and/or Oligomeric Glycidyl Ethers IA Glycidyl ether IA from example 3 can, immediately after the preparation and without further purification, be mixed with a stoichiometric amount of an aminic curing agent. The curing agent used can, for example, be IPDA, TETA or polyetheramine D230. For comparison, corresponding stoichiometric mixtures of bisphenol A based epoxy resin (BADGE; Epilox A19-03 from LEUNA Harze, EEW 182 g/eq) and the aminic curing agents can be prepared. For the rheological characterization, the mixtures can be incubated, for example, at 23° C., 40° C. or 75° C.

The rheological measurements for analysis of the reactivity profile can be conducted on a shear stress-controlled plate-plate rheometer (MCR 301 from Anton Paar) having a plate diameter of, for example, 15 mm and a gap distance of, for example, 0.25 mm at the different temperatures.

The measurement of the gelation time can be conducted in rotating/oscillating mode on the above-specified rheometer at, for example, 23° C. and 75° C. The point of intersection of loss modulus (G") and storage modulus (G') gives the gelation time. The mean viscosity between 2 to 5 min after production of the mixture can be regarded as the starting viscosity.

The measurement of the glass transition temperature (Tg) can be determined by means of DSC analysis (Differential Scanning calorimetry) of the curing reaction to ASTM D 3418 in the 2nd run.

Example 6

Preparation of Cured Epoxy Resin from Monomeric and/or Oligomeric Glycidyl Ethers IB Glycidyl ethers IB for example 4 can be used and characterized in accordance with example 5.

The invention claimed is:

1. A glycidyl ether selected from the group consisting of a glycidyl ether of formula I

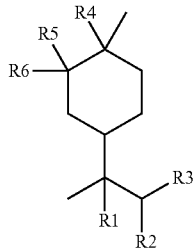

(I)

and an oligomeric glycidyl ether thereof,
where
R1=H and R2=CH$_2$OA and R3=H, or
R1=H and R2=CH$_2$OA and R3=CR7R8OA, or
R1=CH$_2$OA and R2=H and R3=H,
and where
R4=H and R5=CH$_2$OA and R6=H, or
R4=H and R5=CH$_2$OA and R6=CR7R8OA, or
R4=CH$_2$OA and R5=H and R6=H,
and where
A is a glycidyl group or a hydrogen atom, and
R7 and R8 are each independently a hydrogen atom or a C$_1$-C$_4$-alkyl group,
and where
at least 2 A radicals are each a glycidyl group,
and where
when the glycidyl ether is the oligomeric glycidyl ether, the oligomeric glycidyl ether forms through an intermolecular reaction of glycidylated radicals with non-glycidylated radicals comprising a hydroxyl group in the monomeric glycidyl ether of the formula I and a partially glycidylated or non-glycidylated derivative thereof with ring opening of the oxirane ring, where the hydroxyl group which forms through the ring-opening of the oxirane ring in the oligomeric glycidyl ether is optionally in a glycidylated form, and where the oligomeric glycidyl ether has an oligomerization level of 2 to 100 and comprises, by average, at least 1.3 glycidyl groups.

2. The glycidyl ether according to claim 1,
where
R1=H and R2=CH$_2$OA and R3=H, or
R1=CH$_2$OA and R2=H and R3=H,
and where
R4=H and R5=CH$_2$OA and R6=H, or
R4=CH$_2$OA and R5=H and R6=H,
and where A is a glycidyl group.

3. The glycidyl ether according to claim 1,
where
R3 and R6 are not both simultaneously a hydrogen atom.

4. A process for preparing the glycidyl ether according to claim 2, the process comprising
hydroformulating limonene with a mixture of carbon monoxide and hydrogen in the presence of a hydroformylation catalyst at elevated pressure to give a corresponding dialdehyde, and
catalytically hydrogenating the dialdehyde to give a corresponding diol, and
reacting the diol with epichlorohydrin to give the glycidyl ether.

5. A process for preparing the glycidyl ether according to claim 3, the process comprising
hydroformylating limonene with a mixture of carbon monoxide and hydrogen in the presence of a hydroformylation catalyst at elevated pressure to give a corresponding dialdehyde, and
reacting the dialdehyde with a carbonyl compound of formula R7R8C=O forming a new C—C bond in an aldol reaction to give a corresponding beta-hydroxy aldehyde,
catalytically hydrogenating the beta-hydroxy aldehyde to give a corresponding tri- and tetrahydric alcohols, and
reacting the tri- and tetrahydric alcohols with epichlorohydrin to give the glycidyl ether.

6. A limonene derivative of formula II

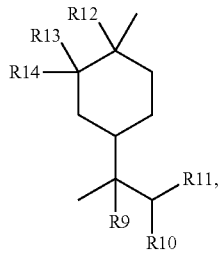

(II)

where
R9=H and R10=CH$_2$OH and R11=H, or
R9=H and R10=CH$_2$OH and R11=CR7R8OH, or
R9=CH$_2$OH and R10=H and R11=H,
and where
R12=H and R13=CH$_2$OH and R14=H, or
R12=H and R13=CH$_2$OH and R14=CR7R8OH, or
R12=CH$_2$OH and R13=H and R14=H,
and where
R7 and R8 are each independently a hydrogen atom or a C$_1$-C$_4$-alkyl group,
and
R11 and R14 are not both simultaneously a hydrogen atom.

7. An oligomer, obtained by a process comprising
reacting the glycidyl ether according to claim 1 with one or more diols,
wherein the glycidyl ether is the glycidyl ether of the formula I.

8. A curable epoxy resin composition, comprising
a curing agent component comprising a curing agent, and
a resin component comprising at least one polyepoxide compound selected from the group consisting of the glycidyl ether according to claim 1 and an oligomer obtained by reacting the glycidyl ether of the formula I with one or more diols.

9. The curable epoxy resin composition according to claim 8, wherein the polyepoxide compound is the glycidyl ether according to claim 1.

10. The curable epoxy resin composition according to claim 8, wherein the curing agent is at least one selected from the group consisting of an amino curing agent and a phenol resin.

11. The curable epoxy resin composition according to claim 8, wherein a portion of the polyepoxide compound is at least 40% by weight, based on an overall weight of the resin component.

12. The curable epoxy resin composition according to claim 8, which comprises bisphenol A- or F-based compounds in a portion of less than 40% by weight, based on an overall weight of the resin component.

13. A process for producing a cured epoxy resin, the process comprising
   curing the curable epoxy resin composition according to claim 8.

14. A cured epoxy resin, obtained by curing the curable epoxy resin composition according to claim 8.

15. A process for producing an adhesive, a composite, a molding, or a coating, the process comprising:
   employing the curable epoxy resin composition according to claim 8 in the process.

* * * * *